(12) United States Patent
See et al.

(10) Patent No.: US 8,313,477 B2
(45) Date of Patent: Nov. 20, 2012

(54) DEVICE AND METHODS FOR MONITORING THE ADMINISTRATION OF A STEM CELL TRANSPLANT

(76) Inventors: Jackie R. See, Fullerton, CA (US); Carl J. Buczek, Santa Ana, CA (US); John W. Matthews, Newport Beach, CA (US)

( * ) Notice: Subject to any disclaimer, the term of this patent is extended or adjusted under 35 U.S.C. 154(b) by 0 days.

(21) Appl. No.: 13/041,307

(22) Filed: Mar. 4, 2011

(65) Prior Publication Data

US 2011/0270060 A1 Nov. 3, 2011

Related U.S. Application Data

(60) Provisional application No. 61/311,105, filed on Mar. 5, 2011.

(51) Int. Cl.
*A61M 31/00* (2006.01)
(52) U.S. Cl. ...................................................... 604/522
(58) Field of Classification Search .......... 604/503–508, 604/522
See application file for complete search history.

(56) References Cited

U.S. PATENT DOCUMENTS

| 4,852,567 | A | | 8/1989 | Sinofsky |
| 5,571,083 | A | * | 11/1996 | Lemelson ..................... 604/522 |
| 6,177,994 | B1 | | 1/2001 | Watson et al. |
| 6,280,703 | B1 | | 8/2001 | Combs et al. |
| 8,096,984 | B2 | * | 1/2012 | Kucharczyk et al. ......... 604/522 |
| 8,147,479 | B1 | * | 4/2012 | Wach et al. .................... 604/522 |
| 8,182,444 | B2 | * | 5/2012 | Uber et al. ....................... 604/66 |
| 2007/0167824 | A1 | | 7/2007 | Lee et al. |
| 2010/0241100 | A1 | * | 9/2010 | Blumenfeld et al. ......... 604/503 |

* cited by examiner

*Primary Examiner* — Kevin C. Sirmons
*Assistant Examiner* — Andrew Gilbert
(74) *Attorney, Agent, or Firm* — The Law Office of Timothy M. Brown

(57) ABSTRACT

A device and methods for the real-time monitoring of stem cells in a stem cell transplant. The device comprises a linear member and particle detection device configured to occupy the lumen of a catheter while the catheter is in place to administer a stem cell transplant to a delivery site in the body of a patient. Monitoring of the stem cells permits the device to provide signals to a computer processor for the determination of one or more characteristics of stem cells in the stem cell transplant.

10 Claims, No Drawings

DEVICE AND METHODS FOR MONITORING THE ADMINISTRATION OF A STEM CELL TRANSPLANT

CROSS-REFERENCE TO RELATED APPLICATIONS

This application claims priority to provisional application Ser. No. 61/311,105, filed Mar. 5, 2011, the contents of which are incorporated by reference in the entirety.

FIELD OF THE INVENTION

The invention is in the field of regenerative stem cell therapy, including devices and methods for monitoring the administration of stem cell transplants through catheters and similar devices.

BACKGROUND

At the time of the invention, there were few technologies for the real-time monitoring of the injection of a stem cell transplant. Magnetic resonance imaging (MRI) allowed for the resolution of stem cells once they were inside the body. However, this method failed to provide any indication of the size or number of cells in the stem cell transplant. Moreover, this method required the stem cells to be labeled (i.e. loaded) with MRI contrast agents such as iron oxide. The use of these imaging agents however alter the biological activity of stem cells and compromise the ability of stem cells to impart a therapeutic effect in the body (see e.g. Cell Transplant. 2009 Dec. 18; and Neuroimage. 2010 Apr. 1;50(2):456-64).

What is needed in the art therefore was a method for the real-time monitoring of the administration of a stem cell transplant which monitors stem cells without the use of contrasting agents which can harm stem cell performance.

SUMMARY OF THE INVENTION

The invention provides a device and methods for monitoring, in real-time, the administration of a stem cell transplant. The device of the invention avoids the use of harmful MRI imaging agents by using a particle detection device to monitor stem cells as the stem cells are being administered to a subject through a catheter. Such monitoring can take place within the catheter lumen, or at the delivery site outside the catheter body.

One aspect of the invention provides a device for the real-time monitoring of a stem cell transplant, wherein the device comprises a linear member capable of occupying the lumen of a catheter, a particle detection device connected to an end of the linear member, wherein the particle detection device is capable of (a) monitoring stem cells that are being administered through the catheter, and (b) conducting a signal based on the monitoring of the stem cells to an external computer processor through the linear member.

One aspect of the invention provides a device for the real-time monitoring of a stem cell transplant, wherein the device comprises a linear member capable of occupying the lumen of a catheter, a light scatter detection device connected to an end of the linear member, wherein the light scatter detection device is capable of (a) monitoring stem cells that are being administered through the catheter, and (b) conducting a signal based on the monitoring of the stem cells to an external computer processor through the linear member.

Another aspect of the invention provides a kit for the real-time monitoring of the administration of a stem cell transplant, wherein the kit comprises a catheter having a distal end and a proximal end with a side port located near the proximal end of the catheter, a linear member comprising at least one fiber optic wire, wherein the linear member has a distal end and a proximal end, a light scatter detection device in contact with the distal end of the linear member, wherein the light scatter detection device comprises at least one light source and at least one optical sensor, said at least on light scatter detection device and said at least one optical sensor being operably connected to the at least one fiber optic wire.

Another aspect of the invention provides a method for monitoring the administration of a stem cell transplant comprising providing a stem cell transplant, providing a catheter, providing a particle detection device, and administering the stem cell transplant to a subject using the catheter while monitoring the stem cell transplant with the particle detection device.

DEFINITIONS

As used herein, the term "stem cell" refers to an undifferentiated cell which has the ability to both self-renew (through mitotic cell division) and undergo differentiation to form a more specialized cell. Stem cells have varying degrees of potency. A precursor cell is but one example of a stem cell.

As used herein, the term "differentiation" refers to the biological process by which a stem cell becomes a more specialized cell type. For example, during embryonic development, pluripotent embryonic stem cells "differentiate" to form multipotent mesenchymal, ectodermal and endodermal stem cells, each of which are limited to a specific developmental pathway (i.e. range of tissues).

As used herein, the term "differentiation potential," "cell potential," "plasticity" and "potential" are used interchangeably herein to refer to the ability of a stem cell to differentiate into one or more specialized cell types. The higher the number of specialized cell types that a stem cell can assume, the greater its differentiation potential.

As used herein, the term "proliferation" refers to an increase in the number of cells in a population by means of mitotic cell division. Proliferation potential refers to a stem cell's (or population of stem cells') ability to grow and divide under suitable culture conditions, such as by unit time (e.g. cell divisions per unit time).

As used herein, the term phenotype refers to an observable characteristic or trait of an organism (e.g. stem cell) such as its morphology, development, biochemical or physiological properties, or behavior. Phenotypes result from the expression of an organism's genes as well as the influence of environmental factors and the interactions between the two. Examples of a stem cell phenotype include, but are in no way limited to, size, cell surface marker profile, proliferation potential, immunogenicity, uncontrolled growth (i.e. tumor cells), plasticity (i.e. differentiation potential), engraftment potential, therapeutic potential, and combinations thereof.

As used herein, the term "stem cell transplant," or "transplant," refers to a composition comprising stem cells that are in contact with (e.g. suspended in) a pharmaceutically acceptable carrier. Such compositions are capable of being administered to a subject through a catheter.

As used herein, the term "pharmaceutically acceptable carrier," or "carrier," refers to any of the well known liquid components useful for immunization such as, for example, culture media and phosphate-buffered saline. Some non-limiting examples of pharmaceutically acceptable carriers include, but are not limited to, those listed in Remington's Pharmaceutical Science (18.sup.th Ed., ed. Gennaro, Mack Publishing Co., Easton, Pa., 1990) and the Handbook of Pharmaceutical Excipients (4.sup.th ed., Ed. Rowe et al. Pharmaceutical Press, Washington, D.C.), each of which is incorporated by reference. "Pharmaceutically acceptable" means that the carrier is non-toxic and does not cause an adverse reaction (e.g. an inflammatory or anergic reaction) when administered to a mammal.

As used herein, the term "particle," or "particulate matter," refers to any phase of a discontinuous material contained within a continuous phase of a supporting medium (e.g. a pharmaceutically acceptable carrier). Either phase may be gaseous, liquid, solid, gel, sol, or combinations thereof. Particles include, for example, cells (e.g. stem cells), nanosomes, vesicles, microspheres (e.g. collagen or other polymer material microspheres, such microspheres seeded with stem cells), microparticles and combinations thereof. The supporting medium may be, for example, a pharmaceutically acceptable carrier.

As used herein, the term "body space" refers to the canals, vessels, ducts, capillaries, passageways, interstitial spaces, and other cavities within the body of a subject.

As used herein, the term "terminal end" refers to the end of a catheter or linear member (e.g. wire) that is inserted into the body, while the teen "proximal end" refers to the opposing end of the catheter or linear means.

As used herein, the term "subject," or "patient," refers to a vertebrate animal, preferably a mammal, and more preferably a human.

As used herein, the term "targeted delivery site," or "delivery site," refers to a location in the body (i.e. body space) where a stem cell transplant or other therapeutic composition is administered in a manner and amount intended to produce a desired therapeutic effect. One skilled in the art will appreciate that suitable delivery sites for stem cell transplants will depend on the condition, disorder or injury that is being treated. Some examples of delivery sites for practicing the invention include, but are not limited to, the circulatory system, the vitreous of the eye, the central nervous system side of the blood brain barrier (e.g. intracranially, intrathecally or intralumbarly), subdermal, subcutaneous, intramuscular, intraperitoneal, intranasal, intraocular, retrobulbar, intracardiac, synovial, intracochlear and combinations thereof. In some embodiments, the delivery site comprises the area within, on, or adjacent to a dysfunctional, diseased or injured tissue. For example, the delivery site may be on, within and/or near a tissue that has been damaged by trauma or an ischemic event (e.g. stroke or myocardial ischemia). A delivery site may, for example, may be on, within and/or near an injured nervous tissue such as the spinal cord or auditory nerves.

As used herein, the term "catheter" refers to any hollow, tubular cannula-type device that is capable of being inserted into canals, vessels, ducts, capillaries, passageways, interstitial spaces, or other cavities in the body, so as to permit the injection or withdrawal of a material from the body. Such catheters include, but are not limited to, those configured to deliver a fluid intravenously, intracranially, intramyocardially, intrathecally, intralumbarly, and/or intraocularly, for example. Non-limiting examples of catheters include, but are not limited to, pulmonary artery catheters, and endobronchial blocker catheters. As used herein, the term "catheter" includes needles and similar devices.

As used herein, the term "catheter space" refers to a space (i.e. void) within a catheter that is capable of ensheathing (i.e. surrounding) a linear member in a manner that permits a linear member (with particle detection device) to be threaded through the catheter towards a targeted delivery site. In catheters that are used in connection with a guide-wire, the catheter space may comprise that area that is intended to be occupied by the guide-wire. The catheter space may comprise, for example, the lumen of a catheter, a guide-wire sheath, and combinations thereof. Examples of catheter spaces include, but are not limited to, those disclosed by the following references, the disclosures of which are incorporated herein by reference: U.S. Pat. Nos. 6,022,319 and 6,228,110.

As used herein, the term the term "light" as used herein refers to radiant electromagnetic energy which may be in the visible or non-visible wavelength(s) range, which is detectable by spectroscopic techniques. The term includes radiant energy at visible, infrared and ultraviolet frequencies. Laser light is one non-limiting example of "light" as the term is used herein.

As used herein, the term "stem cell transplant characteristic," "transplant characteristics," and "characteristic" refer to one or more qualities of a stem cell transplant, such qualities including, but not being limited to, number of stem cells, size distribution of stem cells, size distribution of stem cells and other particles (e.g. cellular debris) in a stem cell transplant, stem cell phenotype, and combinations thereof.

As used herein, the term "monitor," "monitoring," "monitors," and derivatives of such terms, refer to the use of a particle detection device to collect data for the determination of at least one characteristic of stem cells in a stem cell transplant, such characteristics including, but not limited to, stem cell phenotype, size, size distribution, purity, quantity, cell concentration, and combinations thereof.

As used herein, the term "immunogenic" refers to the ability of a substance (e.g. stem cell) to provoke an immune response or the degree to which it provokes a response.

As used herein, the term "tumor" refers to a neoplasm or a solid lesion formed by an abnormal growth of cells (termed neoplastic). A tumor can be benign, pre-malignant or malignant, whereas cancer is by definition malignant.

As used herein, the term "tumor cell" refers to a cell (e.g. stem cell) demonstrating uncontrolled growth, in culture or in vitro. The phenotype of a tumor cell is referred to as "tumorous."

DESCRIPTION

The invention provides devices and methods for monitoring the administration of a stem cell transplant. Such devices may work in coordination with a catheter to provide a means to monitor one or more characteristics of a stem cell transplant as the stem cell transplant is being administered to the body of a subject. These characteristics may be used in a real-time feedback loop to determine or adjust one or more parameters of the administration of the stem cell transplant. The device of the invention further provides a means for determining the phenotype of stem cells in a stem cell transplant. Accordingly, the invention provides a means for optimizing the use of catheters and stem cells in regenerative stem cell therapy.

One non-limiting aspect of the invention provides a device for monitoring the delivery of a stem cell transplant, the device comprising (i) a particle detection device for monitoring stem cells in a stem cell transplant as the stem cell transplant is administered to a delivery site in a subject, (ii) a linear member for positioning the particle detection device at a desired location for monitoring the administration of a stem cell transplant, and (iii) a transmitter for conducting signals from the particle detection device to a computer processor for determining at least one characteristic of the administered stem cell transplant. The linear member and the particle detection device are capable of occupying a catheter space while the catheter is administering a stem cell transplant to the body of a subject. Thus, the linear member and particle detection device are sufficiently small in size so as to occupy the lumen of a catheter, for example, without obstructing the flow of a stem cell transplant through the catheter lumen.

Without being limited to any particular embodiment, the invention may be practiced by providing a catheter, and navigating the catheter to a targeted site in the body of a subject for the administration of a stem cell transplant. Means for navigating (i.e. directing) the catheter to a targeted delivery site are well known in the art and include, for example guide-wire, mapping and catheter-tracking technologies. Once the catheter is positioned at the delivery site in the body of a subject (and guide-wire means withdrawn if so used), a wire (e.g. linear member) connected to a particle detection device is threaded through a catheter space, such as the lumen of the catheter. The guide-wire and linear member (with particle detection device) may enter the catheter lumen through a side port as is well known in the art. Once the particle detection device reaches a desired site (e.g. delivery site) for monitoring the administration of a stem cell transplant, the stem cell transplant is administered to the subject. The stem cell transplant flows through the lumen of the catheter and around the linear member and particle detection device. The particle detection device monitors stem cells in the stem cell transplant as the stem cell transplant flows through the catheter. The particle detection device then conducts signals to an external computer processor through the linear member. The external computer processor then mathematically converts the signals from the particle detection device into one or more stem cell transplant characteristics for interpretation by a human user.

The linear member may take on any construction that permits the linear member to connect to a particle detection device in a manner that allows the linear member (and connected particle detection device) to be threaded through a catheter space while the catheter is positioned within the body of a subject for the administration of a stem cell transplant. In some embodiments of the invention, the linear member comprises at least one fiber optic wire. In such embodiments, the fiber optic wire(s) may be used as a transmitting means for conducting signals from the particle detection device to a computing means. Thus, for example, the invention may comprise a fiber optic wire in communicative contact with a light scatter detection device, wherein the fiber optic wire is capable of conducting signals from the light scatter detection device to a computer processor for the determination of one or more characteristics of a stem cell transplant.

The linear member and particle detection device should be of a sufficiently small diameter so as not to obstruct the administration of stem cells while the linear member occupies the lumen of a catheter. The linear member is preferably of a sufficient length to permit the particle detection device to reach a desired delivery site in the body of a subject.

One aspect of the invention relates to the selection of the particle detection device. As used herein, the term "particle detection device" refers to any device capable of monitoring one or more characteristics of a stem cell transplant as the stem cell transplant is being administered to a subject through a catheter. The particle detection devices of the invention are sufficiently small in size so as to permit them to occupy a catheter space as disclosed herein. Suitable particle detection device for practicing the invention include, but are in no way limited to, devices that collect data relating to electromagnetic energy (e.g. light scatter), mechanical energy (e.g. Brownian motion), acoustic energy (e.g. Doppler devices) and combinations thereof.

In some embodiments of the invention, the particle detection device comprises a light scatter (i.e. diffraction) detection device. Such devices are known in the art and, include devices that measure static (i.e. classical) light scattering, dynamic light scattering and combinations thereof. Light scatter detection devices for use with the invention generally comprise at least one light source and at least one optical sensor. The at least one light source is adapted to provide a source of light incident upon a stem cell transplant as the stem cell transplant is being administered to a subject. The optical sensor(s) is adapted to measure light levels (from the light source(s)) at different scattering angles. The optical sensors then convert the detected light into a signal which is conducted to a computer processor through a linear member (e.g. optical wire or plurality of optical wires). The computer processor then mathematically converts these signals into at least one stem cell transplant characteristic (e.g. quantity and/or size distribution of stem cells, and/or stem cell phenotype). Those skilled in the art will recognize that particle size distribution data obtained from a stem cell transplant may be used to determine the total volume, area or number of stem cells in a predetermined size range contained within a given stem cell transplant.

The invention may be practiced with any light source capable of illuminating a stem cell transplant (within or near a catheter space, or at the delivery site in the body of a subject) with a quantity of light sufficient to be detected by an optical sensor as disclosed herein. Suitable light sources for use with the invention include devices such as lasers which emit monochromatic light. The invention may be practiced with any laser wavelength that creates a detectable, diffracted light signal when the laser illuminates a stem cell transplant within or near a catheter space (e.g. the catheter lumen). The at least one light source may comprise, for example, one or more 420 namometer lasers. In an exemplary non-limiting embodiment of the invention, a 420 nanometer laser may connect to an external power source (e.g. pump laser) through a fiber optic wire which supplies electromagnetic energy to the laser from the power source. Such linear members may comprise a single wire, or bundle of wires which are wrapped (e.g. enclosed) in sheathing material. Such sheathing material should be selected to facilitate the navigation of the fiber optic wires through the catheter, and should be sufficiently thin to avoid the obstruction or collection of stem cells by or within the fiber optic wires.

Light scatter detection devices for use with the invention generally comprise one or more optical sensors for measuring light diffraction resulting from the illumination of the stem transplant by the at least one light source. One skilled in the art will appreciate that like the light source(s), the optical sensors will be of sufficiently small size so as to enable them to occupy a catheter space as disclosed herein. In one specific, non-limiting embodiment of the invention, the optical sensors comprise a 0.5 micron computer microchips having a plurality of variously arranged antennae which are configured to detect scattered light at various angles. Such computer microchips may be designed to detect emissions from light sources including, but not limited to, lasers having wavelengths including, but not limited to, ultraviolet, about 100 nanometers to one millimeter, about 100-400 nanometers, visible light, about 400-750 nanometers, infrared, about 750 nanometers to one millimeter, and combinations thereof. The computer microchip is further arranged to convert light detected by the variously arranged antennae into signals for transmission to a computer processor. Signals from the computer microchip may be connected to a linear member (e.g. optical wire) by an optical coupler in a manner that permits the linear member to transmit signals from the computer microchip to the computer processor. In one non-limiting embodiment of the invention, the optical sensor comprises a sapphire element that is connected to one or more fiber optic (i.e. optical) wires.

Suitable light scatter detection devices for use with the invention are readily available in the art. For example, light scatter detection devices adaptable for use with the invention are disclosed in the following publications, the disclosures of which are incorporated herein by reference: U.S. Pat. Nos. 6,778,271, 6,177,994, 6,104,490, 6,104,491, 6,177,983, 5,164,787, 5,260,764, 4,842,406, 5,416,580; and EP 0 559 529. The invention may similarly be practiced with devices available from commercial light scatter detection device manufacturers, including Malvern™ and MicroTrac™, for example.

One non-limiting embodiment of the invention comprises a light scatter detection device connected to one or more fiber optic wires. The light scatter detection device has one or more lasers connected to the terminal end of the one or more fiber optic wires, said lasers having wavelengths including, but not limited to, ultraviolet, about 100-400 nanometers, visible, about 400-750 nanometers, infrared, about 750 nanometers to one millimeter, and combinations thereof. Although specific laser wavelengths are called out here, one skilled in the art will appreciate that the invention may be practiced with any laser wavelength that permits the detection and monitoring of stem cells as disclosed herein. Each of the one or more lasers may be connected to the one or more fiber optic wires (i.e linear member) by fiber optic couplers as known in the art. Each of the lasers may connect to a single or multiple fiber optic wires. The one or more fiber optic wires are selected and configured to connect to a laser energy source (e.g. pump laser) in a manner that permits the one or more fiber optic wires to conduct energy from the energy source to the one or more lasers connected to the terminal end of the one or more fiber optic wires. Also connected to the terminal end of the one or more fiber optic wires are one or more optical sensors for detecting scattered light that is emitted when a stem cell transplant is illuminated by one or more lasers. Each of the one or more optical sensors is connected to the one or more fiber optic cables by an optical coupler. The optical couplers may be used to connect each sensor to one or a plurality of fiber optic wires. The optical sensors may be dedicated to their own individual fiber optic wire(s), or they may share fiber optic wires with the one or more lasers.

The exemplary device of the preceding paragraph may detect stem cell characteristics either in vitro, or in situ during the administration of a stem cell transplant to a subject. In operation, the terminal end of the device is contacted with a population of stem cells such that the light scatter detection device is permitted to illuminate, and capture reflected light from, the population stem cells. Such contact may occur, for example, by placing the terminal end of the device in a culture dish containing stem cells, a vial of stem cells, or preparation of stem cells in a syringe prior to injection, etc. It is also contemplated that such contact may occur in situ by threading the terminal end of the fiber optic wire(s) (with optical sensor (s) and laser(s) attached thereto) through the lumen of a catheter while the catheter is in position to administer a stem cell transplant to a delivery site in a subject, and administering the stem cells. Once the light scatter detection device is in contact with stem cells, whether in situ or in vitro, the laser energy source (e.g. pump laser) is activated and electromagnetic energy is conducted through the at least one fiber optic wire to the lasers which are then energized and illuminate the stem cells. Light reflected by the stem cells activates the one or more optical sensors to transmit a signal through the one or more optical wires to a computer processor for the determination of one or more stem cell characteristics (including the presence of tumor cells and/or immunogenic cells) using mathematical algorithms and known or readily determined conversion factors obtained by routine in vitro experimentation.

In some aspects of the invention, the particle detection device comprises a Coulter counter. Coulter counters are known in the art as devices for counting and sizing particles and cells. They are used, for example, for bacteria or prokaryotic cells and air quality particle size distributions. In general terms, and without being limited to any particular theory, Coulter counters detect changes in electrical conductance of a small aperture as fluid containing particles (e.g. cells) is drawn through it. Cells, being non-conducting particles, alter the effective cross-section of the conductive channel. Quantitative measurements of the size and concentration of micro- and nano-scale particles may be accomplished using Coulter counters with reduced microchannel size so that particles pass one by one from one chamber to the other. Coulter counters of this design may comprise multiple microchannels to reduce measurement times by counting particles in parallel with one another (i.e. simultaneously).

Suitable Coulter counters for use with the invention are readily available in the art. For example, one skilled in the art will appreciate that the Coulter counters from the following publications may be adapted for use with the invention: U.S. Pat. Nos. 7,397,232 and 7,118,910; Jiang Zhe et al 2007 J. Micromech. Microeng. 17 304-313; Piacentini et al. Conf Proc IEEE Eng Med Biol Soc. 2008;2008:4824-7; Rodriguez-Trujillo et al. Biosens Bioelectron. 2008 Oct. 15;24 (2):290-6; and Zheng et al. Biomed Microdevices 2008 April; 10(2):221-31 (all the foregoing incorporated by reference).

In some embodiments where the particle detection device comprises a light scatter detection device, the linear member may assume a number of wires (e.g. fiber optic wires) which are bundled together and bound by a sheath. Forming the linear member from a plurality of wires performs at least two functions. First, the bundled wires provide a rigid tool for positioning the particle detection device within the body of a subject. Second, a bundle of wires also makes it possible to provide wires that are dedicated to either (a) powering the at least one light source, or (b) transmitting signals from the monitoring means to a computer processor. Without being limited to any particular embodiment, the linear member may comprise, for example, a first set of one or more wires for energizing at least one light source by an external power source, and a second set of one or more wires for transmitting signals from at least one optical sensor, to a computer processor. In such embodiments, the first and second set of wires will be arranged in parallel and optionally wrapped in a sheathing material. Such sheathing material has sufficient flexibility (and rigidity) to permit the linear member to be navigated through the catheter space while the catheter is in position to administer a stem cell transplant to a delivery site in the body of a subject.

As noted above, the particle detection device transmits signals to an external computer processor to allow for the determination of one or more characteristics (i.e. properties) of a stem cell transplant as the stem cell transplant is being administered to a subject. In a preferred embodiment, the computer processor has programming for mathematically converting these signals (in real-time) into one or more stem cell transplant properties (i.e. characteristics) including, but not limited to, the size of stem cells in the stem cell transplant, the quantity of stem cells administered to the subject, the concentration of stem cells in the transplant, the relative size distribution of stem cells in the stem cell transplant, and combinations thereof. Computer processor for converting signals from a light scatter detection device (and their associated programming) include, but are not limited to, those devices disclosed in the following references, the disclosures of which are incorporated herein by reference: U.S. Pat. Nos. 6,778,271, 6,286,376, 6,177,994, 6,281,973, 6,177,983, 6,104,491, and 6,104,490.

As noted above, the invention provides a means for determining the size of stem cells in a stem cell transplant. Determining the size of the cells in the stem cell transplant is advantageous because it provides a means for monitoring the viability and therapeutic potential (i.e. differentiation potential) of the stem cell transplant. Without being limited to any particular theory, stem cell differentiation potential has been shown to be inversely correlated with stem cell size. That is, higher degrees of differentiation and self-renewing potential are correlated with small cell size. For example, human hematopoietic stem cells which are relatively small in size (less than about 10 microns) have cell marker profiles that show they are more primitive than larger cells (between about 10 and 14 microns), both cell types being derived from the same tissue (Blood Jul. 15, 1995; 86 (2);512-523). Thus, detecting the size of stem cells allows the invention to determine the therapeutic potential of stem cells as the stem cells are being administered to a patient. One skilled in the art will appreciate that the different levels of differentiation (i.e. therapeutic) potential for a given cell line (i.e. stem cell transplant) can be determined by routine experimentation, such as by using stem cell surface markers to correlate stem cell size with a specific (e.g. desired) level of differentiation potential.

Monitoring the size of stem cells in the stem cell transplant also allows the viability of the stem cell transplant to be monitored as it is administered to the subject. Stem cells in the stem cell transplant may rupture as a result of preparing the stem cell transplant from stem cells grown in culture, for example. The invention makes it possible to detect ruptured cells in a stem cell transplant by distinguishing whole stem cells, from cellular fragments which are smaller in size than live stem cells. Thus, the size distribution of whole stem cells, and stem cell fragments (e.g. stem cell organelles, chromatin, cell membranes and other cellular debris) may be used to determine the relative number of whole cells in the stem cell transplant.

Monitoring the size of stem cells in the stem cell transplant also provides a means for the classifying the stem cells. For example, knowing the tissue from which the stem cells are derived, and the size of the cells known to be in found in that tissue, one skilled in the art may determine the relative numbers and types of cells that are being administered to a subject. Determining the size distribution of stem cells in a stem cell transplant also allows for the determination of stem cell purity. That is, if the stem cells in a stem cell transplant are varied in sized, the stem cell transplant will have a lower degree of purity of stem cells with a homogenous phenotype.

Monitoring the size of stem cells in the stem cell transplant allows the invention to avoid the administration of clumped cells in stem cell transplantation procedures. Because the invention can distinguish between stem cells of different size, the invention can similarly distinguish between individual cells in suspension, and aggregates of cells which are clumped together. The invention therefore makes it possible to cease the administration of a stem cell transplant if stem cell clusters are detected as the stem cell transplant is being administered to the subject.

The stem cell transplant characteristics monitored by the invention can be used in a feedback loop to adjust the parameters of the administration (i.e. injection) of a stem cell transplant. Such parameters include, but are not limited to, injection rate, injection volume, number of stem cells administered, delivery site, injection pressure and combinations thereof. For example, the particle detection device can transmit signals which allow for the identification of a total number of cells that have been administered to a subject. After a desired quantity of stem cells have been injected, the administration of a stem cell transplant can be stopped. The invention therefore allows for the administration of a precise quantity of stem cells at a selected target site. The invention may similarly be used to administer a desired quantity of cells having a specific level of differentiation potential. This may be accomplished, for example, by monitoring the size of stem cells that are administered to a subject.

It will be appreciated by one skilled in the art that the device of the invention can be used to monitor the size and quantity of stem cells that have been deposited at a delivery site. For example, after the administration of stem cells to the delivery site, the distal end of linear member (e.g. fiber optic wire with light scatter detection device) may be extended through the catheter to occupy the space where the stem cell transplant has been deposited. This permits the light scatter detection device to collect data regarding the size and quantity of stem cells that are occupying the site where a therapeutic effect is desired. In similar fashion, the light scatter device (i.e. particle detection device) may occupy the delivery site as the stem cell transplant is being administered thereby identifying when a desired number of cells have been deposited at the delivery site.

Some aspects of the invention involve using a light scatter detection device to determine the relative purity of a stem cell transplant. Because stem cells of a like phenotype demonstrate like light scattering properties, the invention can be used to determine what proportion of stem cells in a stem cell transplant (i.e. population of stem cells) demonstrates a selected stem cell phenotype. The invention may be practiced in this manner by providing a control population of stem cells having a targeted (e.g. therapeutic) stem cell phenotype, identifying the light scattering signature of the control population of stem cells, and comparing the light scattering signature of the control population of stem cells to the light scattering signature of a stem cell transplant that is intended to be administered to a subject. Higher variation between the light signatures of the control and transplant cell populations will suggest that the transplant contains a relatively greater amount of stem cells having a non-targeted (e.g. non-therapeutic) phenotype. Conversely, smaller variations between the light scattering signatures of the control and transplant stem cell populations will suggest a higher purity of stem cells of having the targeted (i.e. therapeutic) phenotype.

Due to its ability to distinguish between cells of different phenotypes, the device of the invention lends itself to the identification of tumor and/or immunogenic cells. Tumor and immunogenic cells have different light scattering signatures than non-tumor, non-immunogeic stem cells of the same genotype due to the presence of antigen/antibody complexes present on the cell membrane of tumor and/or immunogenic cells. Thus, the presence of tumor and/or immunogenic stem cells in a stem cell transplant can be identified should a tested stem cell transplant exceed a threshold level of deviation from the light scattering signature of a stem cell transplant that is free of non-tumor, non-immunogenic stem cells.

Light scattering detection devices in accordance with the invention may be used to determine the phenotype of a stem cell transplant as it is being administered to a delivery site within the body of a patient (i.e. in situ). This is useful, for example, when the stem cell transplant is being administered to a delivery site (i.e. tissue) that can induce the stem cells in the stem cell transplant to assume an immunogenic and/or tumor phenotype. Such delivery sites may comprise, for example, a tissue defects such as ischemic tissue, traumatized or physically damaged tissue (e.g. damaged myocardium), tumor tissue, infected tissue (e.g. bacterial-, viral-, protazoic-, fungal- or prion-infected tissue), inflamed tissue, infarcted tissue, neurotoxic tissue, genetically deficient tissue, apoptic tissue, necrotic tissue, fibrotic tissue, hibernating tissue, autoimmune-diseased tissue, neovascular tissue, neurodegenerative tissue, and the like. Should the administration of a stem cell transplant at or near such tissue defects cause the cells in the stem cell transplant to assume a tumor and/or immunogenic phenotype, the light scattering signature of the stem cell transplant would immediately change such that the change in phenotype can be detected as the stem cell transplant is being administered to the body of a subject. Having this information, the clinician is permitted to stop the administration of a stem cell transplant to or near a tissue defect so that conversion of the stem cell transplant to a tumor and/or immunogenic phenotype can be avoided and the catheter repositioned if appropriate.

In a non-limiting embodiment of the invention, a laser light scatter detection device for detecting immunogenic and/or tumor stem cells in a stem cell transplant in situ assumes the form of a linear member comprising a length of a 0.014-0.018 inch (diameter) fiber optic wire having on its distal end one or more laser emitting diodes of wavelengths ranging from about 750 nanometers to 1 millimeter. The distal end of the fiber optic also has connected thereon one or more optical sensors (e.g. microchips) configured to capture light from the laser emitting diode(s) as disclosed herein. The fiber optic wire is configured to conduct signals from the optical sensor(s) to an external computer processor which is programmed to convert signals from the optical sensor(s) to identify the relative immunogenicity of and/or presence of tumor stem cells in the stem cell transplant.

In practice, the device of the preceding paragraph may be threaded through the port of a catheter which has been placed in position to deliver a stem cell transplant to a delivery site within the body of a patient. The terminal end of the device, having the laser emitting diode(s) and optical sensor(s), is fed through the catheter lumen until it reaches the distal end of the catheter (e.g. the delivery site). Once in position, the power source is engaged to illuminate the laser emitting diode on the distal of the fiber optic wire. A stem cell transplant may then be administered through the catheter and around the fiber optic wire and light scatter detection device (i.e. laser emitting diode(s) and optical sensor(s)). As the stem cells in the stem cell transplant flow past the light scatter detection device, the stem cells are illuminated and light reflected by the stem cells is captured by the optical sensor(s) thereby conducting signals back to the computer processor where the signals are converted to determine the proportion of stem cells in the stem cell transplant which have a targeted (i.e. therapeutic phenotype). If he catheter is positioned at a site of a tissue defect which causes the stem cells to assume a tumor and/or immunogenic phenotype, the light scatter properties of such stem cells would be immediately altered during their administration such that the change in phenotype could be detected and the administration of the stem cell transplant stopped and the catheter repositioned, if appropriate.

A light scatter detection device capable of detecting stem cell phenotypes as described herein may also be used in vitro to determine the presence of tumor cells and/or the immunogenicity of a stem cell transplant before it is administered to a patient. For example, a light scatter detection device as disclosed herein might be used by contacting the light source on the distal end of a fiber optic wire with a stem cell transplant (in culture for example). Light reflected by the stem cells in the stem cell transplant could then be collected by the optical sensors and communicated to a computer processor as described above. The computer processor could then compare the detected light signals with the light reflection signature of a stem cell transplant that is free of tumor cells and/or immunogenic cells to determine the relative amount of tumor and/or immunogenic cells present in the stem cell transplant.

A light scatter detection device capable of detecting stem cell phenotype as described herein may also find use in cell culture and the preparation of stem cells for transplantation. For example, light scatter signatures may be used to determine when to harvest stem cells for optimal therapeutic efficiency. One skilled in the art might practice such an embodiment by obtaining a light scatter signature for stem cells having a desired phenotype, such as stem cell plasticity, and harvesting the cell when stem cells in culture demonstrate the selected light signature. The device could similarly lend itself to the optimization of stem cell priming just before the stem cells are administered to a subject. That is, the stem cells might be primed until they demonstrate a light scatter signature that is correlated with a targeted therapeutic phenotype.

Some aspects of the invention involve using a light scatter detection device to evaluate an intended delivery site for the administration of a stem cell transplant. Without being limited to any particular theory, some potential delivery sites can present a poor choice for the administration of a stem cell transplant due to the existence of a tissue defect that creates an environment that is harmful to the engraftment and therapeutic efficacy of stem cells. Such tissue defects include, but are in no way limited to, ischemic tissue, traumatized or physically damaged tissue (e.g. damaged myocardium), tumor tissue, infected tissue (e.g. bacterial-, viral-, protazoic-, fungal- or prion-infected tissue), inflamed tissue, infarcted tissue, neurotoxic tissue, genetically deficient tissue, apoptic tissue, necrotic tissue, fibrotic tissue, hibernating tissue, autoimmune-diseased tissue, nevascular tissue, neurodegenerative tissue, and the like.

Accordingly, the term "hostile environment" refers to that area at or near a tissue defect that impairs the biological effect of a stem cell when the stem cell is placed at or near the tissue defect during the administration of a stem cell transplant. Such decreased biological effects including, but not limited to, decreased differentiation potential (i.e. less plasticity), decreased engraftment potential, decreased migration potential, decreased therapeutic efficacy, altered cell surface antigen expression, decreased cell growth factor expression, decreased viability, decreased mitochondrial function, increased apoptosis, increased senescence, and induced retroviral expression. A decrease in biological effect is that measurable decrease of biological activity that can be observed in the presence of tissue defect, compared to the biological activity that is observed in the absence of the tissue defect. The light scatter detection devices of the invention may be used to detect hostile environments prior to the administration of a stem cell transplant so that the administration of the stem cell transplant to such a site may be avoided.

As noted above, catheters for use with the invention may be navigated to a delivery site in the body through the use of a guide-wire. Suitable guide-wire devices for use with the invention include those in the following publications, the entire disclosures of which are incorporated herein by reference: U.S. Pat. Nos. 4,989,608, 4,827,931, 5,042,486, 5,154,179, 5,211,165, 5,271,400, 5,391,199, 6,587,706, 6,560,475, 6,606,513, and 7,505,808; Daniel et al. SMRM Abstr. 1997; 1928; Bornert et al. SMRM Abstr. 1997; 1925; Dumoulin et al. Mag Reson Med 1993; 29: 411-415; Ackerman et al. SMRM Abstr 1986; 1131; Coutts et al., Magnetic Resonance in Medicine 1998, 40:908-13). It is also contemplated that the guide-wire may be directed to a delivery site in the body of a subject through the use of mapping systems, such as a 64 slice CT scanner. Suitable mapping systems for planning the movement of a guide-wire and its associated detecting means are provided in the following publications, the disclosures of which are incorporated herein by reference: U.S. Pat. Nos. 6,134,003, 6,248,074, 5,081,993, and 6,690,963. In some aspects of the invention, the catheter is guided to a desired delivery site through the use of a 64 slice CT scanner.

One specific, non-limiting application of the invention comprises monitoring of the administration of a neural stem cell transplant in the treatment of hearing loss. Such applications may be practiced by selecting a targeted site for the delivery of the neural stem cell transplant such as, for example, the cochlear apparatus or the spinal organ of corti. A catheter is then guided through the body of a subject to the spinal organ of corti. The catheter may enter the body through the femoral, or external iliac artery, for example, whereupon it is guided to the targeted delivery site through the use of a guide-wire and mapping means comprising a 64 slice CT scanner, for example. Once the terminal (i.e. distal) opening of the catheter is positioned at the delivery site, the guide-wire is withdrawn from the catheter. The device of the invention is then introduced to the catheter. Such device may comprise, for example, (i) at least one light source comprising a 420 nanometer laser connected to the terminal end of a first set of one or more 0.018 inch diameter nitinol type wires, wherein the first set of one or more fiber optic wires connects the at least one 420 nanometer laser to a external power source, (ii) at least one detecting means comprising at least one microchip having an antennae for receiving light signals from the at least one 420 nanometer laser; and (iii) a transmitting means comprising a second set of at least one fiber optic wire, wherein the second set of at least one fiber optic wire is connected to the at least one microchip in a manner that permits the at least one microchip to conduct signals to an external computer processor through the second set of at least one fiber optic wire, (iv) wherein the first and second set of at least one fiber optic wires are arranged in parallel and wrapped in a sheathing material. The device of the invention is then guided through the catheter by threading the distal end of the device, with light source and particle detection device attached, through a catheter space such as the lumen. The device may be threaded through the catheter through the use of a side port, for example. Once the light source and particle detection device are positioned at the point where the administration of the stem cell transplant is to be monitored, a stem cell transplant is injected through the catheter. As the stem cell transplant is administered, the light source (420 nanometer laser) illuminates stem cells in the stem cell transplant causing the stem cells to diffract light at characteristic angles. The optical sensor (e.g. 0.5 micron microchip) then detects the scattered light and transmits signals to a computer processor through the second set of fiber optic wires. The computer processor may then mathematically convert the transmitted signals to define one or more characteristics (e.g. phenotype) of stem cells in the stem cell transplant.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

We claim:

1. A method for monitoring the administration of a stem cell transplant comprising:
   a) contacting a catheter with a delivery site in the body of a patient wherein said catheter comprises a lumen;
   b) placing a linear member having attached thereto a particle detection device within said lumen;
   c) administering a stem cell transplant to said delivery site through said lumen; and
   d) detecting stem cells in said stem cell transplant by said particle detection device within said lumen;
   e) wherein said detecting transmits signals to a computer processor for monitoring the administration of said stem cell transplant.

2. The method of claim 1, wherein said particle detection device detects said stem cells based on light, acoustic energy, ultrasound, and combinations thereof.

3. The method of claim 1, wherein said detecting comprises determining the size of stem cells administered to said delivery site, the size distribution of stem cells administered to said delivery site, the purity of stem cells delivered to said delivery site, the phenotype of stem cells administered to said delivery site, or combinations thereof.

4. The method of claim 3, wherein monitoring said phenotype comprises the determination of tumorous stem cells, immunogenic stem cells, cell surface marker profile, proliferation potential, plasticity, engraftment potential, therapeutic potential, or combinations thereof.

5. The method of claim 1, wherein said detecting is used to determine at least one parameter of administering said stem cell transplant.

6. The method of claim 5, wherein said at least one parameter comprises the number of stem cells administered, the delivery site where the stem cells are administered, injection pressure, the size distribution of stem cells that are administered, the phenotype of the cells that are administered, or combinations thereof.

7. The method of claim 1, wherein said particle detection device comprises a light scatter detection device.

8. The method of claim 7, wherein said light scatter detection device comprises at least one light source and at least one optical sensor.

9. The method of claim 8, wherein said at least one light source comprises at least one laser.

10. The method of claim 9, wherein said at least one light source comprises at least one 420 nanometer wavelength laser.

* * * * *